US006988889B2

(12) United States Patent
Abels et al.

(10) Patent No.: US 6,988,889 B2
(45) Date of Patent: Jan. 24, 2006

(54) CUSTOM-FITTED ORTHODONTIC BRACKET MANUFACTURED BY COMPUTERIZED AND SELECTIVE REMOVAL OF PORTIONS OF A BRACKET

(76) Inventors: Norbert Abels, Alleestrasse 30a, 66424 Homburg (DE); Claus H. Backes, St. Wendeler Strasse 45, 66113 Saarbrücken (DE)

( * ) Notice: Subject to any disclaimer, the term of this patent is extended or adjusted under 35 U.S.C. 154(b) by 233 days.

(21) Appl. No.: 10/382,259

(22) Filed: Mar. 4, 2003

(65) Prior Publication Data

US 2004/0175669 A1    Sep. 9, 2004

(51) Int. Cl.
    *A61C 3/00*    (2006.01)
(52) U.S. Cl. ............................................. 433/24; 433/8
(58) Field of Classification Search ................. 433/24, 433/213, 8
    See application file for complete search history.

(56) References Cited

U.S. PATENT DOCUMENTS

| 3,660,900 | A | * | 5/1972 | Andrews ..................... 433/16 |
| 4,131,472 | A | | 12/1978 | MacDonald, Jr. et al. ... 96/38.3 |
| 5,011,405 | A | | 4/1991 | Lemchen ..................... 433/24 |
| 5,454,717 | A | | 10/1995 | Andreiko et al. ............ 433/24 |
| 5,474,448 | A | | 12/1995 | Andreiko et al. ............ 433/24 |
| 5,533,895 | A | | 7/1996 | Andreiko et al. ............ 433/24 |
| 5,674,337 | A | | 10/1997 | Coombs et al. ............. 156/71 |
| 6,210,162 | B1 | | 4/2001 | Chishti et al. .............. 433/213 |
| 6,217,325 | B1 | | 4/2001 | Chishti et al. .............. 433/24 |
| 6,250,918 | B1 | | 6/2001 | Sachdeva et al. ............ 433/24 |
| 6,309,215 | B1 | | 10/2001 | Phan et al. ................... 433/24 |
| 6,315,553 | B1 | | 11/2001 | Sachdeva et al. ............ 433/24 |
| 6,318,994 | B1 | | 11/2001 | Chishti et al. .............. 433/24 |
| 6,413,084 | B1 | | 7/2002 | Rubbert et al. .............. 433/29 |
| 6,431,870 | B1 | | 8/2002 | Sachdeva .................... 433/213 |
| 6,464,496 | B1 | | 10/2002 | Sachdeva et al. ............ 433/24 |
| 6,471,511 | B1 | | 10/2002 | Chishti et al. .............. 433/24 |
| 6,540,512 | B1 | | 4/2003 | Sachdeva et al. ............ 433/24 |
| 2002/0010568 | A1 | | 1/2002 | Rubbert et al. .............. 703/6 |
| 2002/0028417 | A1 | | 3/2002 | Chapoulaud et al. ........ 433/24 |
| 2003/0056561 | A1 | | 3/2003 | Butscher et al. ............. 72/295 |

FOREIGN PATENT DOCUMENTS

WO    WO 01/85047    11/2001

OTHER PUBLICATIONS

"A New Bracket System for Linqual Orthodontic Treatment"; Part 1: Theoretic Background and Development Journal of Orofacial Orthopedics; Dirk Wiechmann; JOrofac Orthop/Fortschr Kieferorthop 2002, No. 3 pp. 234-245.

* cited by examiner

*Primary Examiner*—John J Wilson
(74) *Attorney, Agent, or Firm*—Workman Nydegger (57) ABSTRACT

Manufacture of custom brackets in which a three-dimensional representation of the teeth is used to remove portions or the base to custom-bit the tooth to a predetermined tooth surface, and/or to remove portions of the bracket to create an archwire slot in order to provide a custom orientation and position of the archwire slot in the bracket. The ideal tooth surface for bracket placement and/or the ideal archwire orientation at that bracket may be determined in a computerized fashion by forming a three-dimensional representation of a ideal corrected position of the teeth, and then determining where the bracket and archwire would need to be placed on each of the misaligned teeth in order to achieve the ideal correction.

28 Claims, 4 Drawing Sheets

CUSTOM-FITTED ORTHODONTIC BRACKET MANUFACTURED BY COMPUTERIZED AND SELECTIVE REMOVAL OF PORTIONS OF A BRACKET

BACKGROUND OF THE INVENTION

1. The Field of the Invention

The present invention relates to orthodontics, and more specifically, to a custom-fitted orthodontic bracket and associated methods and computer program products for manufacturing the orthodontic bracket.

2. Background and Related Art

An individual's jaw, gums and teeth (also referred to herein as an "orthodontic structure") combine to provide a critical function by allowing the individual to mechanically break down food for safer swallowing and more efficient digestion. Sever malformations or mechanical flaws of the individual's orthodontic structure may also interfere (even if only slightly) with the proper articulation of language. The abilities to properly eat and speak fluidly are essential needs of mankind. Any degradation in these abilities may have a significant impact on the affected individual's quality of living.

Also, human beings have varying concerns about their own appearance and how they are perceived by others. In addition, some human beings are sometimes inclined (even if on a subconscious level) to form negative judgments about an individual if the appearance of the individual's teeth varies significantly from an ideal societal norm. Accordingly, individuals with such variances may desire for better conformance of the teeth with societal norms, whether their motivation be for the proper functioning of the orthodontic structure, or whether their motivation be for a better appearance, or a combination thereof.

Orthodontics is a now highly-advanced branch of medicine in which dental practices are implemented to manipulate a patient's orthodontic structure for better function and appearance. In order to perform such manipulation, it is necessary to apply sustained and appropriately-directed forces to the teeth. To apply such forces to the teeth, an orthodontist typically affixes brackets to a patient's teeth using bonding material. The orthodontist then couples an arched wire (often called an "archwire") to the brackets using an archwire slot formed in each of the brackets. Some of the teeth may have the archwire anchored to the correspondence bracket, while other teeth may have brackets that allow for some sliding of the archwire.

In order to achieve movement of teeth towards a desired corrected position, it is not only necessary that sustained force be applied, but also that that force be properly directed to achieve the specific movement desired. This requires the considerable knowledge and expertise held by licensed orthodontists. The orthodontist will use that expertise to properly place the brackets, and to properly bend the arched wire. Despite such expertise, however, while the teeth may generally move towards the corrected position, there may be some slight errors in the forces applied by the arched wire that become apparent from the path of movement of the teeth. Accordingly, it is often necessary for the orthodontist to rebend and reposition the arched wire several times before correction is achieved.

One problem associated with orthodontic brackets is that teeth can have a substantially infinite variety of curvatures. Furthermore, precision fitting of the orthodontic bracket promotes higher bonding strengths of the bracket to the tooth. In order to get a good fit at the bracket tooth interface, the orthodontist conventionally identifies a particular position at which the bracket is to be affixed. The orthodontist then selects a bracket that has the closest base curvature match to the surface from amongst a number of pre-manufactured brackets having different base curvatures.

Since there is only a limited number of bracket base curvatures to select, and an infinite variety of tooth surface curvatures, a perfect match is often elusive. Accordingly, the bond strength between the bracket and tooth is not quite as strong as would be the case if there was a perfect match. Also, additional attention would be needed to fill in the gaps due to the imperfect match with a reliable bonding material such as a cement.

One advanced bracket manufacturing technology involves the formation of a custom-fitted bracket that fits with precision on the actual surface of a tooth. A three-dimensional representation of the current orthodontic structure is first acquired using, for example, a high resolution optical scanner. Then, the brackets are designed and optimally positioned in the computer using the three-dimensional representation. The brackets are then physically formed by first making the bracket form out of wax. For example, rapid prototyping techniques may be used to form such wax structures in layers 0.02 mm thick. A more rigid bracket may then be formed to have an identical structure as the wax structure.

This conventional custom-fitted bracket manufacturing technology allows for the positive formation of a custom-bracket that most often is easy to position since the bracket keys into the appropriate surface of the tooth by sense of feel. However, there are some disadvantages to this manufacturing technique. Specifically, the positive formation of brackets using rapid prototyping techniques can be quite expensive and time-consuming. Often orthodontists cannot afford rapid prototyping equipment so such manufacturing often needs to be performed by an off-site service. In addition, the higher costs associated with rapid prototype manufacturing of brackets is most likely passed onto the patient (or insurer) thereby making custom-bracket use relatively expensive.

Accordingly, what would be advantageous are alternative methods for manufacturing custom-fitted brackets that do not require the positive formation of the bracket.

BRIEF SUMMARY OF THE INVENTION

The foregoing problems with the prior state of the art are overcome by the principles of the present invention, which are directed towards methods for manufacturing custom-brackets that result in better bracket and archwire positioning without using rapid prototyping techniques. A three-dimensional digital representation of the current form of an orthodontic structure such as the teeth is used to identify portions of a bracket that should be removed. The identified bracket portion is then removed using any available mechanism such as precision laser or mechanical cutting. The bracket is formed by the removal of material, rather than the positive formation of material, and is thus a less costly and more timely way of manufacturing custom-fitted brackets.

In one embodiment, portions of the orthodontic bracket base are removed in order to allow for more precise fitting of the bracket to the tooth resulting in a stronger and more reliable bonding to the tooth. A computerized representation of an ideal orthodontic structure may be formed in order to automatically determine an ideal position of the bracket on the teeth. If the surface of the tooth is not spherical or close to spherical, then the orthodontist will be able to feel when the bracket has been correctly position thereby reducing the risk of bracket misplacement.

The correct position of the bracket is a function of the position of the archwire slot. In one embodiment, the archwire slot is already pre-manufactured within the bracket that is to have material cut away. However, that need not be the case. The computer may determine the ideal orientation of the archwire slot and the ideal position of the bracket on the tooth, and then cause the removal of appropriate material from the base and from the archwire slot to form a bracket that keys into the appropriate portion of the tooth while having an ideal and customized archwire slot. Since there is some flexibility in the positioning of the archwire slot, there is also some corresponding flexibility in the ideal placement of the bracket, which may be useful if there are some potential bracket placement positions that are less desirable than others. For example, the flexibility in the positioning of the archwire slot allows for some corresponding flexibility in how the archwire is bent. Accordingly, the archwire slot positions may be selected to allow for better hand-bending of the archwire.

In another embodiment, material is not removed from the base at all. Instead, the computer calculates the archwire slot orientation and position, and then causes the custom archwire slot to be cut from the bracket. The computer may also give the orthodontist some instruction on where to place the bracket given the custom archwire slot orientation and position, and what kind of base curvatures that bracket should have.

On occasion, the surface of the tooth may be spherical or close to spherical making it very difficult, even when using custom-fitted brackets, for the orthodontist to feel when the bracket is keyed into the correct position. In that case, material may be removed from the bracket base such that there are one or more protrusions extending along the cut surface of the base from a permanent portion of the base. These protrusions extend to non-spherical surfaces and are thus helpful in keying the bracket into place. Once the brackets are affixed to the teeth, these protrusions may be removed thereby leaving only the permanent portion of the base. Accordingly, the orthodontist may use a sense of feel even when placing the bracket on substantially spherical surfaces of the tooth.

Additional features and advantages of the invention will be set forth in the description that follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The principles of the present invention involve the formation of custom-fitted brackets through the precision removal of material from a pre-manufactured bracket. Material may be removed from the base portion in order to custom-fit the bracket to the appropriate position of the tooth, and/or may be removed from the archwire portion of the bracket in order to allow for customized archwire slot orientation. The determination of what material to remove may be accomplished by acquiring a three-dimensional representation of the teeth, then identifying where the brackets should be ideally placed on the teeth and/or how the archwire should be oriented on each bracket.

Embodiments within the scope of the present invention include computer-readable media for carrying or having computer-executable instructions or data structures stored thereon. Such computer-readable media can be any available media which can be accessed by a general purpose or special purpose computer. By way of example, and not limitation, such computer-readable media can comprise physical computer-readable media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer.

When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, any instructions and data which cause a general purpose computer, special purpose computer, or special purpose processing device to perform a certain function or group of functions. The computer-executable instruction may be, for example, binaries, intermediate format instructions such as assembly language, or even source code. In accordance with the present invention, such computer-executable instructions may be used to assist users in the practice of orthodontics.

Figure 1A:
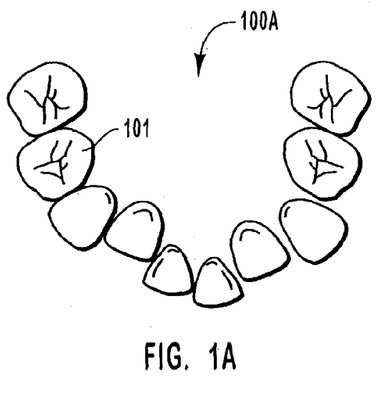
FIG. 1A illustrates a top view of a misaligned lower orthodontic structure.
Figure 1B:
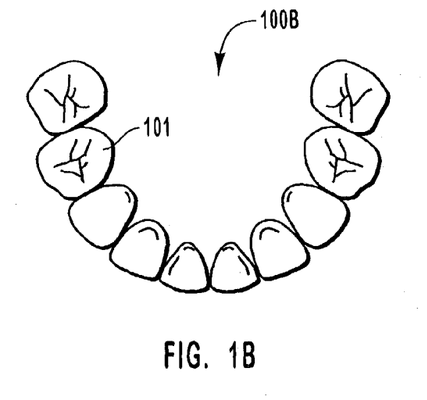
FIG. 1B illustrates a top view of a corrected lower orthodontic structure.

Orthodontics is a branch of dentistry that involves the correction of misaligned or incorrectly positioned teeth. FIG. 1A illustrates a top view of uncorrected lower teeth 100A, while FIG. 1B illustrates a top view of corrected lower teeth 100B. Note that a number of the teeth in the uncorrected lower teeth 100A are misaligned or mispositioned as compared to their ideal position shown in FIG. 1B. In addition to the horizontal movement apparent from the top view, there may also be movement vertically in order to align the teeth along an occlusal plane. The occlusal plan is the imaginary surface on which upper and lower teeth meet.

Corrections such as those illustrated in FIG. 1B as compared to FIG. 1A, may be accomplished by applying precise forces to the teeth over extended periods of time. The teeth respond to such forces by gradually moving and rotating in the direction urged by the applied forces. One conventional method for applying such forces over a sustained period of time is to affix rigid brackets to each of the teeth. An archwire that is formed of resilient material may then be bent and inserted into an archwire slot formed within each bracket. The archwire may be anchored to the brackets of some of the teeth (e.g., the most posterior molars), while being permitted to slide within the archwire slots of the remaining teeth.

The archwire has tendencies to return to its original undeformed position. Accordingly, the archwire will urge the teeth towards a position that results in the archwire attaining the archwire's original position. The position and orientation of the brackets on the teeth and the shape of the archwire are carefully planned by the orthodontists so that the archwire urges the teeth towards an ideal corrected position. Accordingly, it is critical that brackets be correctly positioned on a tooth and remain affixed until orthodontic correction is achieved.

Figure 2:
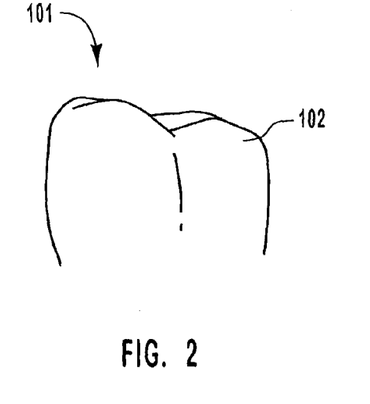
FIG. 2 illustrates a tooth upon which an orthodontic bracket is to be positioned.

FIG. 2 illustrates one of the teeth labeled 101 in FIGS. 1A and 1B in further detail. One problem associated with securely attaching a bracket to a tooth is that teeth may have a wide variety of curvatures. For example, the tooth 101 has a surface 102 that has a particular form and curvature that varies with position on the surface. The shape of the tooth surface on other teeth, and even on the same tooth in different patients, may vary significantly.

In order to accommodate the variety in curvatures on the different tooth surfaces upon which a bracket may be affixed, a given type or brand of bracket may come as a set of preprogrammed brackets having a wide, but standard and finite, variety of different base curvatures. The orthodontics may then match the bracket with the best base curvature with the position on the tooth surface that the bracket base is to be applied to. Although this can often give a good fit of the bracket onto the base, there are only a finite number of base curvatures to accommodate an infinite variety of possible tooth curvatures. Accordingly, there will always likely be some space between the tooth surface and the bracket base since the fit will almost always be inexact. This space may be filled by a bonding material such as light-cured or chemical-cured resin. However, a better fit between the bracket base and the tooth surface usually results in a stronger bond of the bracket to the tooth.

Figure 3:
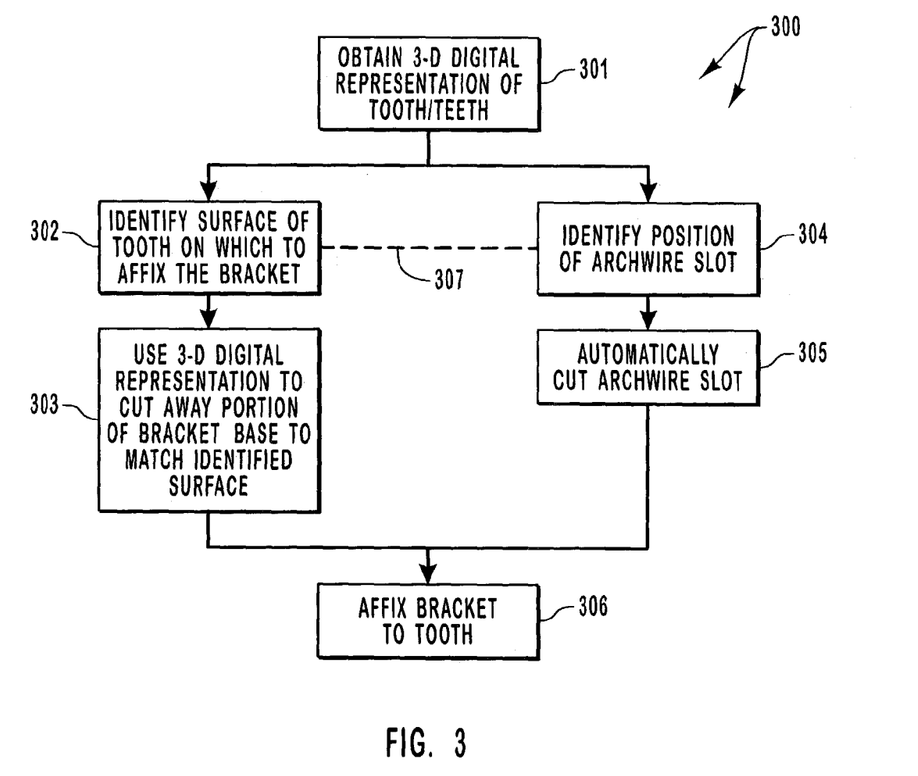
FIG. 3 illustrates a flowchart of a method for custom-fitting a bracket to a tooth in accordance with the principles of the present invention.

FIG. 3 illustrates a flowchart of a method 300 for manufacturing a bracket base that is custom fitted to a tooth. The method 300 of FIG. 3 may be accomplished by system 400 illustrated in FIG. 4. Accordingly, the method of FIG. 3 will be described with frequent reference to the system of FIG. 4.

By custom fitting the bracket base to the bonding surface of the tooth using the method 300 of FIG. 3, the bonding strength is increased and a more suitable base for mechanical bonding may be obtained. This reduces the chance that the bracket will become detached from the tooth during treatment. Avoiding detachment is important since additional time and resources are required to rebond the bracket to the tooth. In addition, during the time that the bracket is detached, the tooth may move towards a less ideal position since ideal movement was predicated on the assumption that all brackets were affixed to the teeth.

Figure 4:
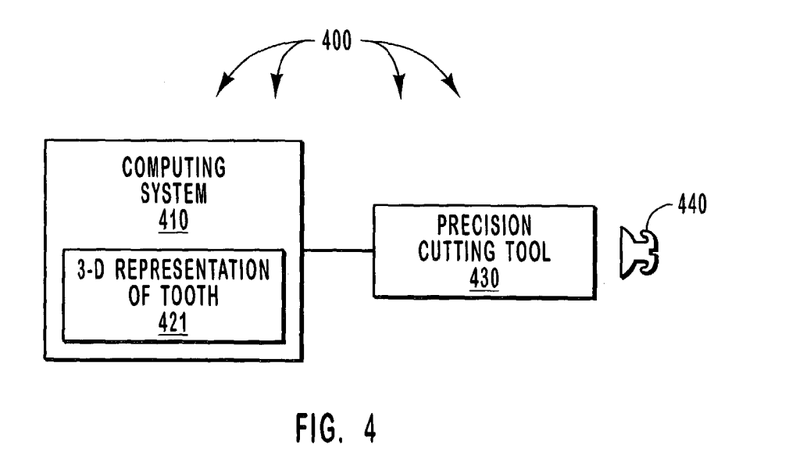
FIG. 4 illustrates a schematic view of a system that manufactures the custom-fitted brackets in accordance with the principles of the present invention.

The method 300 begins with an act of obtaining a three-dimensional digital representation of a tooth upon which a bracket base is to be affixed (act 301). This may be accomplished using conventional methods of, for example, scanning the tooth and then importing the scan results into a Computer-Aided Design (CAD) program as is well known to those of ordinary skill in the art. For example, the system 400 includes a computing system 410 that may be running the CAD program and that has a three-dimensional representation of the tooth 421. Conventional tooth scanning techniques can obtain three-dimensional images of teeth down to very fine resolutions. Accordingly, the three-dimensional representation of the tooth 421 may be quite detailed. The three-dimensional representation of the tooth 421 may be in any three-dimensional format such as, for example, Virtual Reality Markup Language (VRML).

Referring back to FIG. 3, the method 300 also includes an act of identifying a surface of the tooth on which the bracket is to be affixed (act 302). This may be done by having an orthodontist or other user manually select a bonding surface of the tooth from the three-dimensional representation of the tooth based on their own experience and judgment. Alternatively, or in addition, the computing system 410 may calculate an appropriate bonding position relative to the archwire slot so that when other brackets are also position in their calculated positions with the archwire correctly attached, the archwire moves the teeth towards the corrected position. If the archwire slot were pre-manufactured into the bracket, then the computing system may consider the position of the archwire slot when identifying the ideal position of the bracket on the tooth. Systems that provide an ideal position of a bracket on a tooth in order to provide correction are known to those of ordinary skill in the art.

The method 300 then includes an act of using the three-dimensional digital representation of the tooth to direct cutting away of portions of the bracket base until a cut surface of the bracket is shaped to fit a surface of the tooth. For example, the system 400 includes a precision cutting tool 430 which may be directed by the computing system 410 to cut away portions of the base of the bracket 440 until the bracket base is shaped to key into the identified surface of the tooth. This may be accomplished by aligning any pre-manufactured slot to its ideal position, and then allowing the intersection of the bracket with the tooth to define the ideal cut surface of the bracket base. The precision cutting tool 430 may be a laser cutting tool, a precision mechanical cutting tool, or any other cutting tool capable of receiving instructions to cut away specific area(s) of an object.

Figure 5:
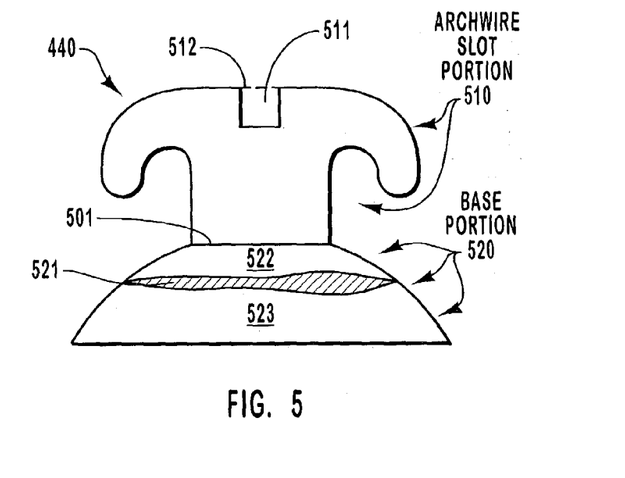
FIG. 5 illustrates an orthodontic bracket in which an illustrated portion of the bracket base is to be removed in order to custom-fit the tooth.

FIG. 5 illustrates the bracket 440 of FIG. 4 in further detail. The bracket includes an archwire slot portion 510 and a base portion 520 which are illustrated as being connected at line 501. Line 501 may be only conceptual if the archwire slot portion 510 and the base portion 520 are formed by molding out of common material. Line 501 may also represent a fused bonded interface if the archwire slot portion 510 and the base portion 520 are composed of different materials. The base portion 520 of the bracket includes a portion to be removed 523 and a portion that is to remain 522 after the cutting.

The cut surface 521 is then ideally shaped to key onto the surface 102 of the tooth 101. Accordingly, the cut surface of the bracket base may then be affixed to the identified surface of the tooth (act 306). Since the bracket base will much more closely fit onto the surface of the tooth, the orthodontist may key the bracket into place thereby being able to feel the bracket as it is moved into its correct position. This is significant as the correct positioning of the bracket is important to the ideal movement of the teeth to its corrected position. Furthermore, the custom-fitting of the bracket to its bonded surface of the tooth improves bonding strength, especially when the bracket has retentive undercutting to allow for even greater bonding strength.

In one embodiment, the archwire slot 511 of the archwire slot portion 510 of the bracket 440 may be pre-manufactured as mentioned above. However, in another embodiment, the archwire slot may not have been pre-manufactured at all, and instead, may not be present in the bracket 440 before precision cutting. For example, referring to the bracket 440 of FIG. 5, the archwire portion 510 may have a surface 512 in which there is no archwire slot pre-formed in the bracket.

Instead, the computer may consider the position of the archwire as being an addition degree of freedom for use when identifying where to place the bracket on the surface of the tooth. This interdependence between the identification of a position and orientation of the archwire slot, and the identification of the position of the bracket is represented in FIG. 3 by the dashed line 307.

By selecting a slightly different position for the archwire slot as compared to its position if pre-manufactured, then the ideal bracket position may also be shifted as well. This may prove useful in moving the ideal bracket placement away from the gums or some other surface of the tooth which may be difficult for bracket positioning. For example, if in one archwire slot position, the ideal calculated bracket position would be on a substantially spherical surface of the tooth, the computer may consider moving the proposed archwire position until the ideal bracket position on the tooth is moved to a less spherical surface of the tooth. Accordingly, the orthodontist would feel the bracket key into place more distinctly. Furthermore, the flexibility in the positioning of the archwire slot allows for some corresponding flexibility in how the archwire is bent. Accordingly, the archwire slot positions may be selected to allow for better hand-bending of the archwire so that the archwire is in one plane once the teeth achieve the corrected position.

In this embodiment, the method 300 may also include an act of identifying a position of an archwire slot that when the cut surface of the bracket base is affixed to the tooth would result in better alignment of the teeth (act 304). Then, the archwire slot may automatically be cut in the archwire slot portion of the bracket at the identified position of the archwire slot (act 305).

Whether or not the archwire slot is pre-manufactured or custom precision cut, if the bracket base is to be applied to a relatively spherical surface, the orthodontist may have difficulty placing the bracket in its proper position by a sense of feel. In this case, the computer (or an associated user) may opt to generate temporary protrusions along the cut surface that extend in at least one direction to portions of the tooth that are not spherical. The orthodontist may then more distinctly and easily key and bond the bracket into place. The protrusions from the cut surface may then be removed since their primary purpose was to help the orthodontist place the brackets by sense of feel, not necessarily to hold the bracket in place during treatment.

Figure 6:
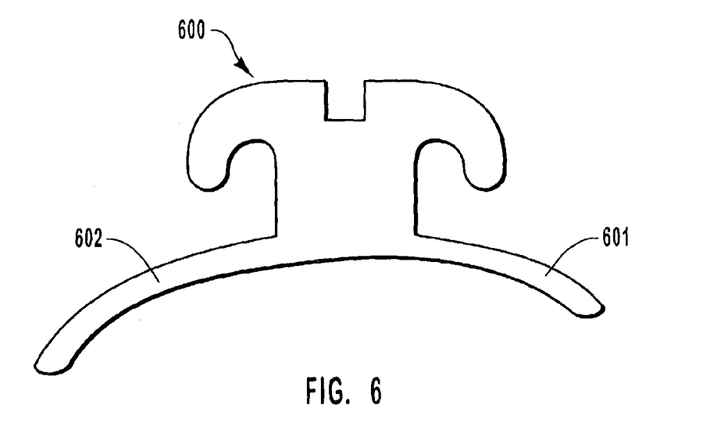
FIG. 6 illustrates a bracket that has two protrusions extending along the cut surface that contacts the tooth to thereby allowing for keying of the bracket into place even if the main portion of the cut surface is to be placed on a relatively spherical tooth surface.

FIG. 6 illustrates an example bracket 600 that appears similar to the bracket 440 illustrated in FIG. 4 except that the bracket is shown with a portion of the base already removed, and in which the cut surface include several finger-shaped protrusions 601 and 602 that extend to non-spherical surfaces of the tooth. Naturally, the size of the bracket base that existed before cutting would need to be larger to accommodate the length of each of the protrusions.

Until now, the description has focused on embodiments of the present invention in which portions of the bracket base are cut away to custom-fit the surface of the tooth. One of the embodiments involve custom-placing the archwire slot as well. In one embodiment that will now be described, the bracket base need not be custom-fit to the tooth at all. Instead, only the archwire slot position is custom-placed. This embodiment may be implemented using pre-manufactured brackets that have different brackets having different preset base curvatures. This embodiment is described with respect to the method 700 illustrated in FIG. 7.

Figure 7:
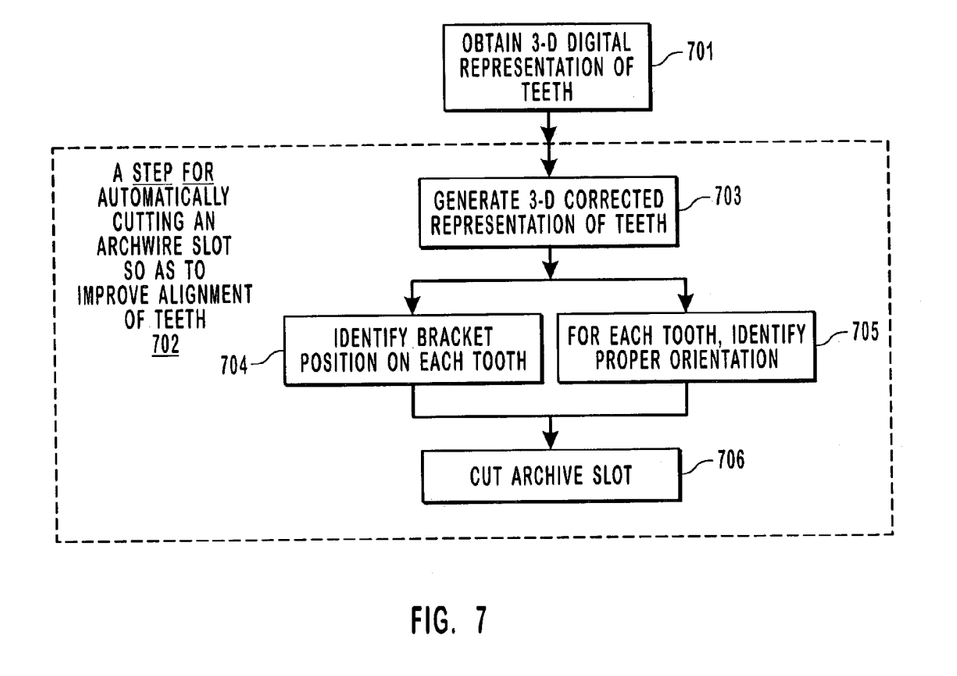
FIG. 7 illustrates a flowchart of a method for manufacturing a bracket that has a custom archwire slot for improved alignment of the teeth in accordance with the principles of the present invention.

After obtaining current three-dimensional digital representation of the teeth upon which a plurality of bracket bases are to be affixed (act 701), the method 700 includes a functional, result-oriented, step for automatically cutting an archwire slot in at least one of the orthodontic brackets so as to improve alignment of the teeth (step 702). This functional, result-oriented step includes any corresponding acts for accomplishing this purpose. In the embodiment of FIG. 7, however, the step 702 includes corresponding acts 703 through 706.

More specifically, the an improved digital representation of the teeth is generated that represents a corrected form of the misaligned teeth (act 703). This may be accomplished using conventional mechanisms in which each individual three-dimensional tooth is moved in the computer program to its ideal position. Then, the position of the orthodontic bracket on each of the teeth is identified (act 704). For each tooth, a proper orientation of the archwire slot that would result in improved alignment is then identified (act 705) given the current three-dimensional representation, the improved digital representation, and the identified position of the bracket on the corresponding tooth. Then, the computer directs the cutting of the archwire slot to obtain the identified orientation of the archwire slot (act 706).

Figure 8:
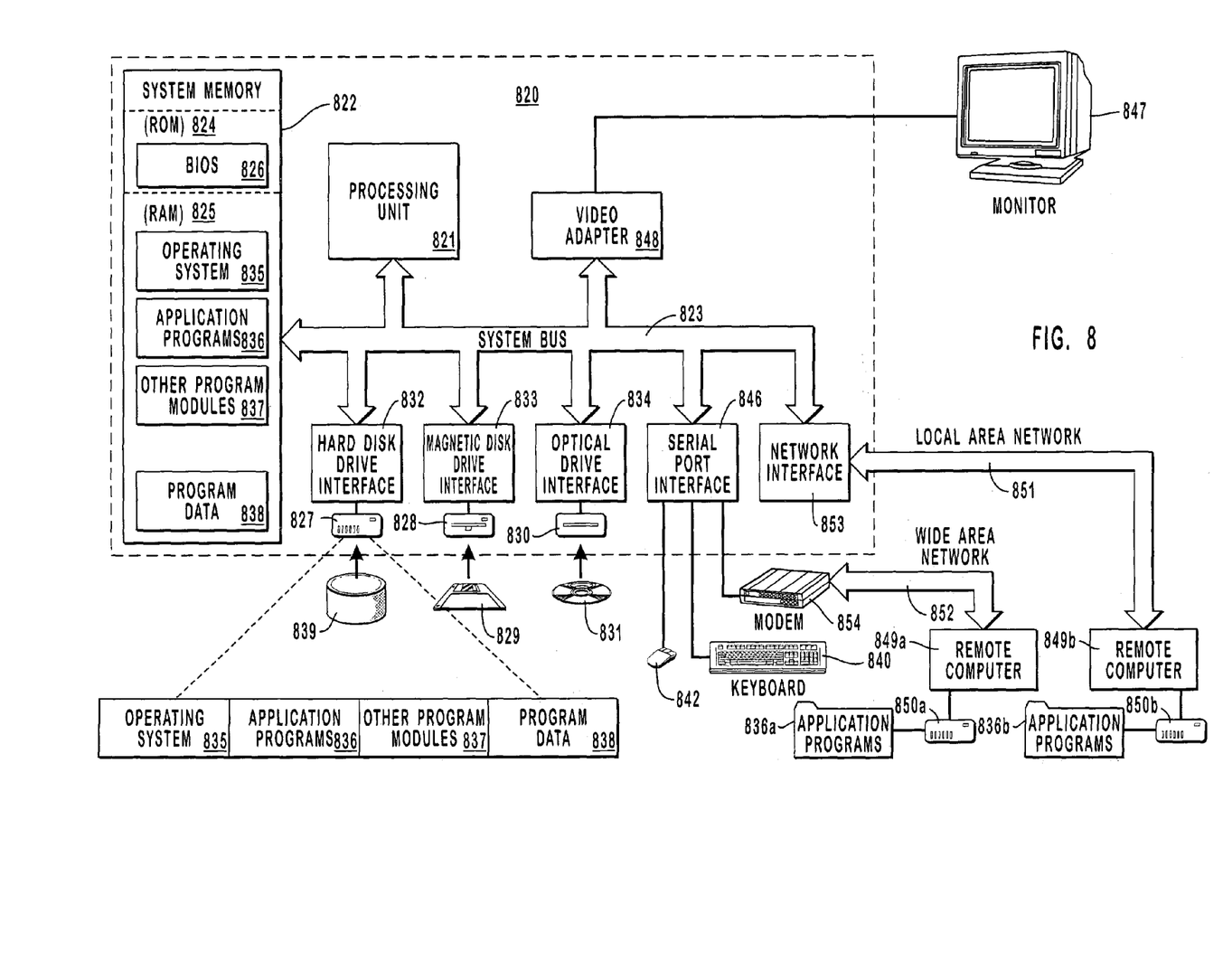
FIG. 8 illustrates a suitable computing environment in which the present invention may be employed.

FIG. 8 and the following discussion are intended to provide a brief, general description of a suitable computing environment in which the invention may be implemented. Although not required, the invention will be described in the general context of computer-executable instructions, such as program modules, being executed by computers in network environments. Generally, program modules include routines, programs, objects, components, data structures, etc. that perform particular tasks or implement particular abstract data types.

With reference to FIG. 8, an exemplary system for implementing the invention includes a general purpose computing device in the form of a conventional computer 820, including a processing unit 821, a system memory 822, and a system bus 823 that couples various system components including the system memory 822 to the processing unit 821. The system bus 823 may be any of several types of bus structures including a memory bus or memory controller, a peripheral bus, and a local bus using any of a variety of bus architectures. The system memory includes read only memory (ROM) 824 and random access memory (RAM) 825. A basic input/output system (BIOS) 826, containing the basic routines that help transfer information between elements within the computer 820, such as during start-up, may be stored in ROM 824.

The computer 820 may also include a magnetic hard disk drive 827 for reading from and writing to a magnetic hard disk 839, a magnetic disk drive 828 for reading from or writing to a removable magnetic disk 829, and an optical disk drive 830 for reading from or writing to removable optical disk 831 such as a CD-ROM or other optical media. The magnetic hard disk drive 827, magnetic disk drive 828, and optical disk drive 830 are connected to the system bus 823 by a hard disk drive interface 832, a magnetic disk drive-interface 833, and an optical drive interface 834, respectively. The drives and their associated computer-readable media provide nonvolatile storage of computer-executable instructions, data structures, program modules and other data for the computer 820. Although the exemplary environment described herein employs a magnetic hard disk 839, a removable magnetic disk 829 and a removable optical disk 831, other types of computer readable media for storing data can be used, including magnetic cassettes, flash memory cards, digital video disks, Bernoulli cartridges, RAMs, ROMs, and the like.

Program code means comprising one or more program modules may be stored on the hard disk 839, magnetic disk 829, optical disk 831, ROM 824 or RAM 825, including an operating system 835, one or more application programs 836, other program modules 837, and program data 838. A user may enter commands and information into the computer 820 through keyboard 840, pointing device 842, or other input devices (not shown), such as a microphone, joy stick, game pad, satellite dish, scanner, or the like. These and other input devices are often connected to the processing unit 821 through a serial port interface 846 coupled to system bus 823. Alternatively, the input devices may be connected by other interfaces, such as a parallel port, a game port or a universal serial bus (USB). A monitor 847 or another display device is also connected to system bus 823 via an interface, such as video adapter 848. In addition to the monitor, personal computers typically include other peripheral output devices (not shown), such as speakers and printers.

The computer 820 may operate in a networked environment using logical connections to one or more remote computers, such as remote computers 849*a* and 849*b*. Remote computers 849*a* and 849*b* may each be another personal computer, a server, a router, a network PC, a peer device or other common network node, and typically include many or all of the elements described above relative to the computer 820, although only memory storage devices 850*a* and 850*b* and their associated application programs 836*a* and 836*b* have been illustrated in FIG. 8. The logical connections depicted in FIG. 8 include a local area network (LAN) 851 and a wide area network (WAN) 852 that are presented here by way of example and not limitation. Such networking environments are commonplace in office-wide or enterprise-wide computer networks, intranets and the Internet.

When used in a LAN networking environment, the computer 820 is connected to the local network 851 through a network interface or adapter 853. When used in a WAN networking environment, the computer 820 may include a modem 854, a wireless link, or other means for establishing communications over the wide area network 852, such as the Internet. The modem 854, which may be internal or external, is connected to the system bus 823 via the serial port interface 846. In a networked environment, program modules depicted relative to the computer 820, or portions thereof, may be stored in the remote memory storage device. It will be appreciated that the network connections shown are exemplary and other means of establishing communications over wide area network 852 may be used.

Those skilled in the art will appreciate that the invention may be practiced in network computing environments with many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes, which come within the meaning and range of equivalency of the claims, are to be embraced within their scope.

The invention claimed is:

1. A method for manufacturing a bracket base that is custom fitted to a tooth comprising the following:
   an act of obtaining a three-dimensional digital representation of a tooth upon which a bracket base is to be affixed; and
   an act of using the three-dimensional digital representation of the tooth to direct cutting away of portions of the bracket base until a cut surface of the bracket is shaped to fit a surface of the tooth, so that a main portion of the cut surface is approximately spherical, the cut surface also including at least one protrusion that is cut to extend along the surface of the tooth to a portion of the tooth that is less spherical.

2. A method in accordance with claim 1, further comprising the following:
   an act of affixing the cut surface of the bracket base to the surface of the tooth.

3. A method in accordance with claim 2, further comprising:
   an act of removing the at least one protrusion after the act of affixing the cut surface of the bracket base to the surface of the tooth.

4. A method in accordance with claim 1, wherein the act of using the three-dimensional digital representation of the tooth to direct cutting comprises the following:
   an act of using the three-dimensional digital representation of the tooth to guide a laser to cut away the portions of the bracket base.

5. A method in accordance with claim 1, wherein the act of using the three-dimensional digital representation of the tooth to direct cutting comprises the following:
   an act of using the three-dimensional digital representation of the tooth to guide a mechanical cutter to cut away the portions of the bracket base.

6. A method in accordance with claim 1, wherein the act of obtaining a three-dimensional digital representation of a tooth upon which a bracket base is to be affixed comprises the following:
   an act of scanning the tooth; and
   an act of formulating the three-dimensional digital representation of the tooth based on the results of the act of scanning.

7. A method in accordance with claim 1, further comprising the following:
   an act of identifying a surface of the tooth that would result in a better alignment of the teeth if the bracket base is affixed to the identified surface, wherein the cut surface of the bracket bases fits to the identified surface of the tooth.

8. A method in accordance with claim 7, wherein the bracket base is coupled to an archwire slot portion of the bracket, the archwire slot portion having an archwire slot formed therein, wherein the act of identifying a surface of the tooth takes into consideration a position of the archwire slot.

9. A method in accordance with claim 7, wherein the bracket base is coupled to an archwire slot portion of the bracket, the method further comprising:
   an act of identifying a position of an archwire slot that when the cut surface of the bracket base is affixed to the tooth would result in better alignment of the teeth; and
   an act of automatically cutting the archwire slot in the archwire slot portion of the bracket at the identified position of the archwire slot.

10. A method in accordance with claim 1, further comprising the following:
   an act of affixing the cut surface of the bracket base to the surface of the tooth.

11. A computer program product for manufacturing a bracket base that is custom fitted to a tooth, the computer program product comprising one or more tangible computer-readable media have thereon the following:
   computer-executable instructions for obtaining a three-dimensional digital representation of a tooth upon which a bracket base is to be affixed; and
   computer-executable instructions for using the three-dimensional digital representation of the tooth to direct cutting away of portions of the bracket base until a cut surface of the bracket is shaped to fit a surface of the tooth, so that a main portion of the cut surface is approximately spherical, the cut surface also including at least one protrusion that is cut to extend along the surface of the tooth to a portion of the tooth that is less spherical.

12. A computer program product in accordance with claim 11, wherein the media comprises mass storage media.

13. A computer program product in accordance with claim 11, wherein the media comprises system memory.

14. A computer program product in accordance with claim 11, wherein the computer-executable instructions for using the three-dimensional digital representation of the tooth to direct cutting comprise the following:
   computer-executable instructions for using the three-dimensional digital representation of the tooth to guide a laser to cut away the portions of the bracket base.

15. A computer program product in accordance with claim 11, wherein the act of computer-executable instructions for using the three-dimensional digital representation of the tooth to direct cutting comprise the following:
   computer-executable instructions for using the three-dimensional digital representation of the tooth to guide a mechanical cutter to cut away the portions of the bracket base.

16. A computer program product in accordance with claim 11, wherein the computer-executable instructions for obtaining a three-dimensional digital representation of a tooth upon which a bracket base is to be affixed comprise the following:
   computer-executable instructions for formulating the three-dimensional digital representation of the tooth based on scanning results.

17. A computer-program product in accordance with claim 11, wherein the one or more computer-readable media further have thereon the following:
   computer-executable instructions for identifying a surface of the tooth that would result in a better alignment of the teeth if the bracket base is affixed to the identified surface, wherein the cut surface of the bracket bases fits to the identified surface of the tooth.

18. A method for manufacturing an orthodontic bracket for improved alignment of the teeth comprising the following:
   an act of obtaining current three-dimensional digital representation of the teeth upon which a plurality of bracket bases are to be affixed;
   an act of generating an improved digital representation of to teeth that represents better alignment of the teeth;
   an act of identifying a position of an orthodontic bracket on each of a plurality of the teeth; and
   for at least one of the orthodontic brackets, performing the following:
      an act of using the three-dimensional digital representation of the tooth to direct cutting away of portions of the bracket base until a cut surface of the bracket is shaped to fit a surface of the tooth, so that a main portion of the cut surface is approximately spherical, the cut surface also including at least one protrusion that is cut to extend along the surface of the tooth to a portion of the tooth that is less spherical;
      an act of identifying an orientation of an archwire slot to be formed in the orthodontic bracket given the current three-dimensional representation, the improved digital representation, and the identified position of the bracket on the corresponding tooth; and
      an act of performing computerized direction of the cutting of the archwire slot to obtain the identified orientation of the archwire slot.

19. A method in accordance with claim 18, wherein the act of performing computerized direction of the cutting of the archwire slot comprises the following:
   an act of directing a laser cutter to cut the archwire slot.

20. A method in accordance with claim 18, wherein the act of performing computerized direction of the cutting of the archwire slot comprises the following:
   an act of directing a mechanical cutter to cut the archwire slot.

21. A method in accordance with claim 18, wherein the act of obtaining a current three-dimensional digital representation of the teeth upon which a plurality of bracket bases are to be affixed comprises the following:
   an act of scanning the three; and
   an act of formulating the current three-dimensional digital representation of the teeth based on the results of the act of scanning.

22. A method for manufacturing an orthodontic bracket for improved alignment of the teeth comprising the following:
- an act of obtaining current three-dimensional digital representation of the teeth upon which a plurality of bracket bases are to be affixed; and
- a step for automatically cutting an archwire slot in at least one of the orthodontic brackets so as to improve alignment of the teeth, so that a main portion of the cut surface is approximately spherical, the cut surface also including at least one protrusion that is cut to extend along the surface of the tooth to a portion of the tooth that is less spherical.

23. A method in accordance with claim 22, wherein the step for automatically cutting an archwire slot in at least one of the orthodontic brackets so as to improve alignment of the teeth comprises the following:
- an act of generating an improved digital representation of the teeth that represents better alignment of the teeth;
- an act of identifying a position of an orthodontic bracket on each of a plurality of the teeth; and
- for at least one of the orthodontic brackets, performing the following:
  - an act of identifying an orientation of an archwire slot to be formed in the orthodontic bracket given the current three-dimensional representation, the improved digital representation, and the identified position of the bracket on the corresponding tooth; and
  - an act of performing computerized direction of the cutting of the archwire slot to obtain the identified orientation of the archwire slot.

24. A computer program product for manufacturing an orthodontic bracket for improved alignment of the teeth, the computer program product comprising one or more tangible computer-readable media having thereon the following;
- computer-executable instructions for obtaining current three-dimensional digital representation of the teeth upon which a plurality of bracket bases are to be affixed;
- computer-executable instructions for generating an improved digital representation of the teeth that represents better alignment of the teeth;
- computer-executable instructions for identifying a position of an orthodontic bracket on each of a plurality of the teeth; and
- for at least one of the orthodontic brackets, computer-executable instructions for performing the following:
  - using the three-dimensional digital representation of the tooth to performing computerized direction for cutting away of portions of the bracket base until a cut surface of the bracket is shaped to fit a surface of the tooth, so that a main portion of the cut surface is approximately spherical, the cut surface also including at least one protrusion that is cut to extend along the surface of the tooth to a portion of the tooth that is less spherical;
  - identifying an orientation of an archwire slot to be formed in the orthodontic bracket given the current three-dimensional representation, the improved digital representation, and the identified position of the bracket on the corresponding tooth; and
  - performing computerized direction of the cutting of the archwire slot to obtain the identified orientation of the archwire slot.

25. A computer program product in accordance with claim 24, wherein the computer-executable instruction for performing computerized direction of the cutting of the archwire slot comprise the following:
- computer-executable instructions for directing a laser cutter to cut the archwire slot.

26. A computer program product in accordance with claim 24, wherein the computer-executable instruction for performing computerized direction of the cutting of the archwire slot comprise the following:
- computer-executable instructions for directing a mechanical cutter to cut the archwire slot.

27. A computer program product in accordance with claim 24, wherein the media comprises mass storage media.

28. A computer program product in accordance with claim 24, wherein the media comprises system memory.

* * * * *

UNITED STATES PATENT AND TRADEMARK OFFICE
CERTIFICATE OF CORRECTION

PATENT NO. : 6,988,889 B2  Page 1 of 1
APPLICATION NO. : 10/382259
DATED : January 24, 2006
INVENTOR(S) : Norbert Abels and Claus H. Backes It is certified that error appears in the above-identified patent and that said Letters Patent is hereby corrected as shown below:

Title Page
Item 57, ABSTRACT, line 3, before "the base" change "or" to --for--
Item 57, ABSTRACT, line 3, change "custom-fit the tooth" to --custom-fit the bracket--

Column 1
Line 31, before "better" remove [for]

Column 4
Line 18, change "allowing" to --allow--

Column 11
Line 39, after "media" insert --that--

Column 12
Line 29, before "teeth" change "to" to --the--

Signed and Sealed this

First Day of August, 2006

JON W. DUDAS
*Director of the United States Patent and Trademark Office*